United States Patent [19]

Sundrehagen

[11] Patent Number: 5,919,708

[45] Date of Patent: *Jul. 6, 1999

[54] ASSAY FOR GLYCATED BLOOD PROTEINS

[75] Inventor: Erling Sundrehagen, Oslo, Norway

[73] Assignee: Axis Biochemicals AS, Oslo, Norway

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/570,569

[22] Filed: Dec. 11, 1995

Related U.S. Application Data

[62] Division of application No. 08/050,274, filed as application No. PCT/EP91/02163, Nov. 13, 1991.

[30] Foreign Application Priority Data

Nov. 14, 1990 [GB] United Kingdom .................. 9024771

[51] Int. Cl.$^6$ ..................................................... G01N 33/72
[52] U.S. Cl. ........................... 436/66; 436/161; 436/166; 436/175; 436/177; 436/536; 436/815; 436/824; 436/539
[58] Field of Search .................................. 436/66, 67, 87, 436/88, 161, 166, 175, 177, 815, 824, 172, 178, 536, 539

[56] References Cited

U.S. PATENT DOCUMENTS

| 4,268,270 | 5/1981 | Gabbay et al. . | |
|---|---|---|---|
| 4,269,605 | 5/1981 | Dean et al. | 436/87 |
| 4,701,418 | 10/1987 | Katapodis . | |
| 4,861,728 | 8/1989 | Wagner . | |
| 5,240,735 | 8/1993 | Lau | 436/87 |
| 5,242,842 | 9/1993 | Sundrehagen . | |

FOREIGN PATENT DOCUMENTS

| 0 455 225 | 11/1991 | European Pat. Off. . |
|---|---|---|
| 3 720 736 | 1/1989 | Germany . |
| 88 00346 | 1/1988 | WIPO . |
| 90 13818 | 11/1990 | WIPO . |

OTHER PUBLICATIONS

Schleicher et al., *J. Clin. Chem. Clin. Biochem.*, vol. 29, 577–587 (1989).

Hayashi et al., *Clin. Chem. Acta.*, vol. 149, 13–19 (1985).

*Primary Examiner*—Jeffrey Snay
*Attorney, Agent, or Firm*—Bacon & Thomas, PLLC

[57] ABSTRACT

A method of assessing glycated blood protein in a sample which comprises separating glycated and non-glycated protein using a liquid phase precipitation reagent, contacting the sample with a signal forming agent capable of binding preferentially to the glycated protein, and assessing the signal forming agents.

28 Claims, No Drawings

ASSAY FOR GLYCATED BLOOD PROTEINS

This application is a division of application Ser. No. 08/050,274, filed May 13, 1993, now U.S. Pat. No. 5,506,144 which is a 371 of PCT/EP91/02163.

This invention relates to a ligand binding assay for the assessment of glycated blood proteins (GBPs).

It has long been known that many glucoproteins in body tissues and fluids occur as a result of non-enzymatic reactions of body proteins with sugars. These non-enzymatically glycosylated proteins are referred to herein as glycated proteins.

As mammalian tissue appears to contain no enzyme capable of reversing the glycation reaction, the extent to which any given protein is glycated is essentially dependent on the inherent ability of the protein to undergo glycation,
the lifetime of the protein within the body, and
the glucose concentrations to which the protein has been exposed.

Accordingly, unlike direct measurements of glucose concentration in body tissue or body fluid samples (e.g. blood, plasma or urine), which give information only about the glucose concentration at the time of sampling, the degree of glycation of a protein provides an indication of the body's control of glucose concentration averaged over a longer period of time.

In patients with unstabilized diabetes mellitus, the degree of protein glycation is frequently several times higher than in normoglycemic patients, and as a result, several GBP assays have been proposed as screens for diabetes mellitus or as means by which a patient's medium to long term control over blood glucose levels may be evaluated.

Such assays have been proposed for glycated haemoglobin (GH) and glycated serum albumin (GSA) in particular as the relatively long lifetimes of these proteins provide an indication of the long and medium term control of blood glucose and as these proteins are both abundant and relatively prone to glycation. Thus GSA and GH levels reflect the body's control over blood glucose during the previous 1–3 weeks and 1–3 months respectively.

GBP assays generally rely on the separation out of the GBP from a body fluid or tissue sample, on the binding to the GBP in such a sample of a detectable label, e.g. a chromophore, a fluorophore or a radiolabel, or on a chemical degradation of the GBP in such a sample, e.g. oxidation of the fructoseamine moiety in alkaline conditions in the presence of a redox indicator. Such assays and their advantages and disadvantages were reviewed by Schleicher et al in J. Clin. Chem. Clin. Biochem. 27: 577–587 (1989).

Prior art methods are known which involve separation of the glycated protein from the non-glycated protein by means of ion exchange chromatography. This was the method first proposed for GH assays and is the clinical method most commonly used. However, it is expensive and time consuming and results are influenced by small temperature variations.

Several further assays have involved the use of boronic acid derivatives to isolate or label the glycated proteins in a sample. It has long been known that while boronic acids form esters with carbohydrate moieties having cis-diol residues, such as glycated proteins, enzymatically formed glycoproteins do not form such esters. Thus chemically immobilized boronic acids have been proposed for use in isolation of glycated proteins by affinity chromatography and the use of such materials to quantify the glycated fraction of hemoglobin was proposed for example by Dean et al in GB-A-2024829.

The use of such columns however is expensive and time-consuming and for GBPs other than GH Schleicher (supra) warns that the degree of binding of the glycated protein is very sensitive to the conditions under which chromatography is effected.

The reaction in the liquid phase of glycated proteins with chrmphore or fluorophore labelled boronic acids has also been proposed as the basis for an assay for glycated proteins, in particular GH. Thus Schleicher in DE-A-3720736 proposed an assay relying on one of the following three principles for measurement of the total glycated protein present in a sample:

1. a shift in the absorption maximum of a boronic acid chromophore label when bound to a glycated protein,
2. a polarization change of fluorescence in a boronic acid fluorophore label when bound to a glycated protein, or
3. measurement of the amount of chromophore or fluorophore labelled boronic acid bound to glycated protein after removal of excess unbound labelled boronic acid, e.g. using activated charcoal.

None of those methods however can be used for the quantitation of a specific GBP. In addition the reagents proposed by Schleicher have rather low absorption coefficients and their absorption maxima lie rather close to that of hemoglobin making it difficult or impossible to detect GH.

Wagner, in U.S. Pat. No. 4,861,728, proposed an assay for GH which involves separating out the GH by contacting a hemolysate sample with a solid support onto which is bound an antibody specific for total hemoglobin and reacting the GH with a fluorophore labelled boronic acid. Total bound hemoglobin can than be measured reflectometrically while bound GH levels can be estimated fluoroscopically.

However this technique suffers from the drawback that the association constants between the glycated hemoglobin and the boronic acid labels are rather low (i.e. $10^3$ to $10^5$ mol$^{-1}$) and, since the effective concentration of GH is rather low when immobilized, binding of the label is also correspondingly reduced.

There is thus a continuing need for GBP assays that are rapid, simple, inexpensive and readily adapted for use in clinical laboratories or by diagnosticians.

One such assay, for GH, is described[]in our application WO-A-90/13818 and we have now appreciated that that technique is readily adaptable for use as a assay for other GBPs, most particularly GA.

Thus viewed from one aspect the present invention provides a method of assessing a glycated blood protein in a sample, said method comprising the steps of a) optionally hemolysing said sample to liberate cell bound glycated protein;

b) separating said glycated blood protein and the corresponding non-glycated blood protein from said sample using a liquid phase precipitation reagent;

c) contacting said sample before or during separation of said glycated and non-glycated proteins therefrom or contacting said separated proteins with a first signal forming agent capable of binding to said glycated protein with substantially higher binding affinity than for the corresponding non-glycated protein;

d) optionally, contacting said sample before or during separation of said glycated and non-glycated proteins therefrom or contacting said separated proteins with a second signal forming agent capable of binding to said glycated protein and to said corresponding non-glycated protein; and e) assessing the signal forming agents which have bound to said separated proteins and/or which have not bound to said glycated protein or said corresponding non-glycated protein;

with the proviso that where said glycated protein comprises glycated hemoglobin said first signal forming agent is a chromophore labelled boronic acid or salt thereof having an absorption maximum at above 600 nm.

In the assay method of the invention, the glycated protein which is labelled by the first signal forming agent may be any one, or indeed any set, of the blood proteins. However, for the method to provide an indication as to blood glucose control over a particular time period, it is preferably arranged so that assessment is substantially only of one specific glycated protein, especially hemoglobin, albumin, complement C3, fibrinogen or transferrin.

In one particularly preferred embodiment of the invention at least two first signal forming agents are used, each being substantially specific for a different GBP, the signal for each being sufficiently different for them to be measured without significant interference with each other. Thus for example the first signal forming agents might conveniently comprise a chromophore labelled antibody or antigen-binding antibody fragment specific for one GBP and a fluorophore labelled or radiolabelled antibody or fragment specific for another GBP. Preferably however, for ease of measurement, labelling will be with distinguishable labels of the same type, e.g. both (or all) being chromophores. This; embodiment may require more than one agent to be used to effect separation of the two or more proteins under assay—however in many cases a single agent or separation means will suffice. In this embodiment to obtain an indication of the relative abundance of the glycated forms of the proteins under assay it will also be desirable to utilize two or more protein specific second signal forming agents. By appropriate selection of the proteins under assay, e.g. hemoglobin and albumin and optionally also complement C3 or fibrinogen, this embodiment of the invention allows a single assay to provide an indication of the history of the patient's blood glucose control over the short, medium and long (up to 3 months) term. Where the glycated protein being assessed is labelled with a chromophore, the particular agent used will preferably have an absorption maximum above 600 nm so that the method can be performed on erythrocyte or hemoglobin containing samples, e.g. whole blood, without requiring the hemoglobin to be washed away. Likewise if a second signal forming agent is used to label both the glycated and non-glycated forms of the protein being assayed, as will desirably be the case where the protein is other than hemoglobin, then if that agent includes al chromophore it will also preferably have an absorption maximum above 600 nm.

A range of chromophore labels and compounds carrying them suitable for use as first or second signal forming agents in the method of the invention is disclosed in our copending British Patent Application No. 9024775.0 filed Nov. 14, 1990 and entitled Chemical Compounds and in the corresponding international patent application (published as WO-A-92/08722) a copy of the text of which is filed herewith and the disclosures thereof are incorporated herein by reference. These compounds contain chromophores having absorption maxima above 600 nm, e.g. phenoxazine and phenothiazine derivatives carrying secondary or tertiary amino and imino groups at the 3 and 7 positions. These chromophores conveniently function as first signal forming agents where they are linked to boronic acid moieties in the manner discussed in greater detail below, e.g. by substitution of the amino moiety by a 3-(N-ethyl-piperidin-4-yl-carbonylamino) phenylboronic acid grouping (attached at the β carbon of the N-ethyl moiety). Particularly preferred such chromophores include chloroaluminium-phthalocyanines such as those defined and disclosed in the copending application.

In addition to determining the level of a glycated protein within a sample, in carrying out the method of the invention it may also be desirable to obtain an assessment of the level of glycated and non-glycated protein present and to calculate a ratio of glycated to total protein.

It may also be particularly desirable to obtain an indication of total protein concentration in the blood for the specific protein under assay as the degree of glycation may vary with total protein concentration for patients suffering from conditions which result in abnormally low concentations of the protein under assay.

The protein separating step does not require the separation of the total amount of glycated protein and non-glycated protein present in the sample. It is sufficient for only a proportion of both the glycated and non-glycated fractions to be separated as long as the method is appropriately calibrated. Such calibrations are routine in clinical laboratory assays.

As used herein the term "assessing" is intended to include both quantitation in the sense of obtaining an absolute value for the amount of glycated or total protein in a sample, and also obtaining an index, ratio, percentage or similar indication of the level of glycated protein, for example relative to the total protein concentration of the sample.

It will be appreciated that the new method of the invention avoids the separation of the glycated from the non-glycated protein fraction, but relies instead on a separation of both glycated and non-glycated protein from a sample. Consequently there is no need for the first signal-forming agent to be immobilised since it need not be used as part of a separation system, and indeed it is preferred that it is not immobilised.

The method of the invention may be used to assess the amount of glycated protein in samples of blood, blood hemolysates or blood extracts, both from healthy individuals and from patients suffering from or suspected to suffer from diabetes mellitus. The samples may be in dry, liquid or frozen form before analysis. Hemolysates for analysis by the method of the invention may be prepared for example using different kinds of reagents to hemolyse and expose the carbohydrate moieties of the glycated proteins to the binding reactions. This treatment can be performed prior to or in combination with the use of the other reagents necessary for the performance of this method. Optionally to reduce interference the samples may be treated to reduce the levels of free or weakly bound glucose, e.g. using glucose oxidase or a buffering solution with a pH below 6.

In the method of the invention, the reaction of the signal-forming agents with the protein may take place before, during or after the protein separation from the sample. The order chosen depends on the chemical equipment or instruments to be used for the performance of the method and what is found more practical.

In one preferred embodiment of the invention the binding of the signal forming agent and the protein isolation takes place simultaneously in a homogeneous solution, from which the protein is precipitated and isolated by centrifugation or filtration. However, reaction and separation conditions may have to be chosen within the limitations of the glycosyl residue—boronic acid association constants, which are rather low ($10^3$–$10^5$ mol$^{-1}$.l).

From the strength of the signal obtained from the signal forming agents, the concentration of the signal forming molecules bound to or separated with the proteins may be determined. An "absolute" standard for quantitation of glycated proteins does not yet exist; however if desired a calibration or correlation of this new method to prior art methods may be obtained using standard protein solutions containing known concentrations of the glycated form of the protein as determined by prior art method(s).

In the method of the invention, the first and second signal forming agents may bind specifically to the protein under assay or may be agents which serve to label other proteins. In the latter case, the separation in the method of the invention should be such as, in one or more steps, to separate the protein under assay out from the sample substantially free of other proteins labelled by the signal forming agents.

Where the protein under assay is separated from the sample by a precipitation or by an immobilizing agent specific for that protein, then the first signal forming agent may conveniently comprise phenyl boronic acid linked to a signal forming label either directly, by an amine or amide linkage, by a spacing moiety or by any kind of chemical linkage known in the art, which leaves the dihydroxyboryl residues free to react with the cis-diol residues of the glycosyl moieties of the glycated protein. Dependent on which pKa value of the boronic acid residues is desired the phenyl ring may be further substituted, for example by nitro, formyl or alkoxy groups or by other substituents which influence the pKa-value, but do not sterically interfere with the binding to the cis-diol residues of the glycated protein.

The boronic acid residues which may be used for the synthesis of the first signal forming agent of the present invention are conveniently synthesized from aminophenyl, for example m-aminophenyl, boronic-acid residues, and the linkage to the label or signal forming part of the said signal forming molecules or conjugates; is typically achieved by means of diazonium ion formation, silanization, by use of coupling agents such as glutardialdehydes, carbodiimides, cyanogen halides, succinimides or any other coupling agents taught in the general chemical literature. The signal forming label is attached in a manner leaving the boronic acid residue free to react with the cis-diols of the glycated protein analyte and may be "activated" beforehand in order to render it reactive with amine or other reactive moieties on the dihydroxyboryl residues e.g. dimethylaminoazobenzene isothiocyanate and dimethylamino-naphthalene sulphonyl chloride. The first signal forming agent may also be further modified to increase water solubility.

The signal-forming dihydroxyboryl agents for use in accordance with the invention are preferably in a non-immobilized form, and may comprise boronic acid or other specific or non-specific binding residues linked, directly or indirectly, to chemical structures (labels) being able, directly or indirectly, to form signals, that can be used for chemical or physical quantitation purposes.

The signal forming label may comprise enzyme(s), preferably enzymes not carrying carbohydrate cis-diol moieties or depleted with respect to fractions carrying cis-diol residues. Alternatively, the signal forming label may be partially or totally constituted by coloured or fluorescent moieties (chromophores or fluorophores). A large range of coloured, fluorescent or pigmented compounds suitable for use as labels are known in the art and may be used. Suitable examples include anthraquinones, azodyes, azine dyes such as oxazines and thiazines, triazines, naturally occurring pigments such as porphyrins, phycobiliproteins, including phycoerythrins and phycocyanins, chlorophylls, and their analogues and derivatives, carotenoids, acrinidines, xanthenes, including fluoresceins and rhodamines, indigodyes, thioxanthenes, coumarines, polymethines, including di- and tri- arylmethines, and derivatives thereof and phthalocyanines and metal phthalocyanines, optionally linked by spacing moieties interposed between the signal forming label and the boronic acid residues, which are left free to react with the cis-diols of the glycated protein under assay.

Similarly, a wide range of radioactive compounds may be used as the signal forming label part of the agents used in this invention, among them $^{125}I$ labelled compounds. Such labelled compounds may conveniently be obtained by $^{125}I$-labelling of the carbon ring of the phenyl boronic acids or by conjugating aminophenylboronic acid to $^{125}I$-labelled reagents, e.g. the well known Bolton-Hunter reagent. A review of such radiolabelling techniques is given by Bolton in Biochem. J. 133: 529–539 (1973). In the performance of the method of this invention, rather high concentrations of reactants are necessary, thus in many embodiments of this invention the $^{125}I$-labelled conjugates can be mixed with non-radioactive boric acid or boronic acids with identical or different structure, to obtain a radioactivity of the assay reagents at an appropriate level.

Alternatively, a boronic acid residue may be conjugated to natural or synthetic compounds which can produce a chemiluminescent signal which may be assayed in known manner (see Cormier, M. J. et al, "Chemiluminescence and Bioluminescence", Plenum Press,. New York 1973). Suitable chemiluminescent compounds include luciferin, oxalic esters, 1,2-dioxethane, luminol or derivatives thereof, but are not limited to these. If appropriate hydrogen peroxide, enzymes e.g. luciferase, or other chemicals may be used to produce the chemiluminescent signal from the signal forming agents used.

A particularly suitable example which of a labelled boronic acid which may be used as the first signal forming agent is the conjugate obtained by reaction of fluorescein isothiocyanate with aminophenyl boronic acid, resulting in a conjugate with a free carboxylic moiety. Other suitable conjugates include aminophenylboronic acid conjugated to chloroaluminium phthalocyanine or fluorescein, e.g by means of 1-ethyl-3(3-dimethylaminopropyl)-carbodiimide (EDC), and fluorescein isothiocyanate having blocked carboxyl groups or where the carboxylic acid moiety has been removed conjugated to aminophenylboronic acid. Rhodamine B, conjugated e.g. by means of a carbodiimide, to an aminophenylboronic acid may also be used, however, this conjugate has a rather poor solubility in most solutions of interest for assay by the method of the invention. N-(resorufin-4-carbonyl)-piperidine-4-carboxylicacid-N'-hydroxysuccinimide-ester) (herein after abbreviated to RESOS, a material available from Boehringer Mannheim, Germany) is a signal forming molecule which the inventor has conjugated to aminophenyl boronic acid and which has been shown to exhibit excellent solubility properties. Boronic acid residues,

are often named dihydroxyboryl residues in their electrically neutral form, and form anions by the binding of hydroxyl ions

and may as such form salts. The first signal forming agents used in the method of this invention may comprise residues with one or more of these forms of boronic acid, depending on the pH and electrolyte content of the reagent composition. It is in the anionic form that boronic acids bind to the cis-diol residues of glycated protein.

The use of high molecular weight signal-forming conjugates with boronic acids in the method of this invention is preferably avoided where the glycated protein is hemoglobin because of the limited accessability of the glycated moiety of most glycated hemoglobins; a substantial fraction of the glycated hemoglobin in blood is glycated at the N-terminal valine amino acid of the beta-chain, which is not readily accessible for water-soluble high molecular weight molecules, as described in U.S. Pat. No. 4,658,022. This patent teaches the use of a very significant denaturation to expose the glycated residue to antibody binding reactions.

The method of the present invention is particularly preferably arranged to assay glycated albumin (GA). Albumin has an affinity for a wide range of substances, and this has prompted investigators to describe the biological role of albumin as a vehicle for biologically important ligands. Albumin has several binding sites with different affinities for ligands, for example inorganic cations, organic anions, non-ionic compounds, and specific antibodies or antibody fragments.

Numerous synthetic and exogenous anions bind to albumin, including many organic dyes and pH-indicator substances. These possess a nonionic hydrophobic part and an ionic hydrophilic part which strongly influences the binding to albumin. Both the affinity and the number of binding sites increase in the order: alcohol, carboxylate, sulfonate, sulfate.

Common examples include the fatty acids, but the binding of bilirubin and tryptophan is also of great biological importance.

Nonionic substances known to bind to albumin include steroid hormones, such as testosterone and cortisol.

Binding of inorganic copper(II) to albumin has been described in the literature, and affinity constants have been estimated as $10^7$ mol$^{-1}$l or higher. Both copper, and other metals are known to bind to albumin, e.g. nickel, produce coloured complexes. Thus salts of copper and other metals may be used as the second signal forming agents in the method of the invention. Fluorescent rare-earth ions (e.g. lanthanides, especially Europium and Terbium) and their chelates are especially interesting for use in the method of the invention because of their unique fluorescent properties, high detection sensitivity, and applicability to time-resolved fluorometry. Eu-chelates are used for example in the DELFIA-system of Pharmacia, Sweden. Such chelates may therefore also serve as signal forming agents for albumin assays.

Examples of anionic compounds known to bind to albumin include among several others:

tryptophan/tryptophan derivatives (e.g. N-acetyl-tryptophan) (association constant $K_a$ about $2 \times 10^4$ mol$^{-1}$l)

thyroxine (association constant $K_a$ about $10^6$ mol$^{-1}$l)

fatty acid anions detergents, e.g. dodecyl sulfate (association constant $K_a$ about $1.2 \times 10^6$ mol$^{-1}$l)

bile salts hematin (precursor of bilirubin)

sulfonamides acetamides salicylates and azo dyes.

In general, the binding to albumin is weaker than that of bilirubin (an open chain tetrapyrrole with an association constant $K_a$ of about $10^7$ mol$^{-1}$l) and $C_{16-18}$ fatty acid anions (association constant $K_a$ about $10^7$ mol$^{-1}$l). This is also true for organic dyes, but both the affinity and the number of dye-binding sites is dependent on the nature of the dye. Examples include:

sulfonaphthaleines (association constant $K_a$ about $10^6$ mol$^{-1}$l)

tetrabromo derivatives (e.g. bromocresol green, bromocresol blue, bromosulfophthalein)

naphthalene suilfonate compounds (association constant $K_a$ probably about $10^6$ mol$^{-1}$l)

Evans blue

Trypan blue

Congo red azobenzoates and their derivatives (association constant $K_a > 10^6$ mol$^{-1}$l) and methyl red The binding of porphyrins to albumin is of great biological importance. The binding affinity is high, but some variation is seen between different derivatives. Thus deuteroheme binds more strongly than protoporphyrin and the binding affinity depends on the metal in the center of the porphyrin ring.

The synthetic derivative tetracarboxyphenylporphyrin (TCPP) and the corresponding metalloporphyrins Cu—TCPP and Co—TCPP show the following affinity: Co—TCPP (association constant $K_a$ about $10^{7}$ mol$^{0.1}$l) >CU—TCPP>TCPP and may thus also be used as signal forming agents.

Other organic anions which may be mentioned in this regard include:

methyl orange dinitrophenol fluorescent ligands, such as 1-anilinonaphthalene-8-sulfonate (ANS), naphthalene sulfonate aflatoxins, and acridines (e.g. Rivanol)

Other dyes which may be used as the second signal forming agent, especially in assays for albumin, include Ponceau S, Coomasie brilliant blue and bicinchoninic acid (suitably combined with copper(II) in an alkaline media). Particular mention, for use as the second signal forming agent in assays for glycated blood proteins such as albumin, may also be made of bromophenol blue (absorption maximum 590 nm). For albumin assays the metallaporphyrin Cr(III)-tetracarboxyphenylporphyrin (available from Porphyrin, Products, USA) is also particularly suitable especially if presented in solution buffered to pH 9.0, e.g. using 0.25M ammonium acetate buffer. The compound has an absorption maximum of 440–450 nm, significant absorption up to 600 nm and binds strongly to albumin.

The RESOS-aminophenyl boronic acid conjugate metioned in the examples below and the phthalocyanine, phenoxazine and phenothiazine boronic acid conjugates of our copending British and International Patent applications mentioned above are particularly suitable for use as the first signal forming agent, again especially in assays for glycated albumin.

Separation out of the glycated and non-glycated protein under assay is effected by the action of a precipitating agent, an agent which can if desired also function as a signal forming agent.

In preferred embodiments of the invention, the separation of the protein being assayed (and the signal forming molecules bound thereto) is achieved by selective precipitation of the total protein from homogeneous solutions, e.g. by the use of appropriate precipitation reagents optionally combined with a chromatography, centrifugation or filtration system.

Thus according to the invention the separation of the protein under assay may be effected by means of non-immobilised specific binding proteins such as specific monoclonal or polyclonal antibodies, or any other agent which precipitates the protein being assayed from solution. Monoclonal antibodies reactive to different epitopes or polyclonal antibodies can be used to form a precipitate with the protein. Precipitation can also be obtained by means of secondary antibodies. Preferably antibodies without cis-diol moieties, or depleted with respect to cis-diol containing moieties, or immunoreactive fragments thereof may be used.

However a drawback of this method is that since the association constant of the boronic acid containing signal-forming molecules and the glycosylated residues of glycosylated haemoglobins is only in the order of $10^3$ to $10^5$ $mol^{-1}0.1$, rather high concentrations of reactants are necessary resulting in a rather high consumption of antibodies per test.

In preferred embodiments of the invention protein precipitation from the liquid phase is achieved by the use of metallic cations or organic solvents. The precipitates may easily be separated for example by centrifugation or filtration and the reagents are inexpensive and efficient.

For one such embodiment a specific or close to specific precipitation of hemoglobin from solution has been achieved by the use of certain organic solvents, for example alcohols such as ethanol and/or butanol, ketones such as acetone, ethers, e.g. cyclic ethers such as dioxane and tetrahydrofuran, amide solvents such as dimethylformamide or diethylformamide, sulphoxide solvents such as dimethylsulphoxide, hydrocarbon solvents such as toluene, and halogenated hydrocarbon solvents such as chloroform. When precipitating a whole blood sample, diluted to give approximately 6.5 mg hemoglobin and 1.5 mg HSA/ml, by adding 50% butanol (v/v) in ethanol to a final concentration of 9% butanol (v/v), 94% of the hemoglobin was precipitated and only 1% of the HSA. Such precipitation was obtained without loss of the boronic acids residues bound to cis-diol moieties.

Specific precipitation of hemoglobin may also be achieved using metallic cations binding to and aggregating proteins. Suitable cations include zinc, copper, and less preferably nickel, cobalt and cadmium. This has the important advantage that any hemoglobin precipitated in this way may easily be re-dissolved by adding a solubilising complexing agent. Using zinc ions a substantially specific precipitation of hemoglobin from whole blood hemolysates can be obtained, which is an unexpected observation. By way of example, by using a zinc ion concentration of 2.5–4 mM in presence of 6.5 mg hemoglobin and 1.5 mg HSA/ml, a specific or close to specific hemoglobin precipitation is obtained. However a concentration above 4 mM zinc ions, substantial coprecipitation of HSA occured. This is illustrated by the results indicated below:

| Zn concentration (mM) | % Hb precipitated | % HSA precipitated |
| --- | --- | --- |
| 2.6 | 87 | 6 |
| 3.9 | 87 | 15 |
| 6.5 | 91 | 92 |

The ion concentration must however be carefully adjusted so as not to interfere with any signalforming boronic acid derivatives used. If desired, the precipitated protein may optionally be washed or filtered to remove excess cations before reaction with signal forming boronic acid conjugates.

This reaction sequence is especially preferred when rather anionic signal forming boronic acid conjugates are used, since direct binding between excess zinc ions and the anionic conjugates may result in unwanted interference. In addition to zinc other metallic cations may be used, provided that they do not precipitate on their own in the buffering solution used for the precipitation reaction.

Due to the possibility of the metal ions participating in hydrolysis or other reactions with the other reagents in the test solution, precautions need to be taken to ensure that the metal cations remain soluble and available for the precipitation of the hemoglobin..

Some of the signal-forming boronic acid conjugates described in this specification contain groups which can donate a pair of electrons to the metal cations, and thereby act as complexing agents. This ability to form ligand-metal complexes can be used to control the reactions, keeping the metal ion in solution, preventing the formation of complexes between the metal and the boronic acid signal forming derivatives, and ensuring availablility and high enough concentrations of the metal ion, to give the desired protein precipitation.

Since both ligand concentration and stability constants of different metal complexes need to be considered, appropriate buffer salts may be used to prevent the formation of insoluble metallic complexes (hereinafter referred to as Me-complexes).

Buffer salts forming weak monodentate Me-complexes are therefore preferred and an example of such a buffer is ammonium acetate in combination with zinc, forming soluble Zn(Ac) and $Zn(NH_4)$ complexes.

By adding stronger complexing agents such as multidentate chelating ligands to the buffer, all the said reactions can be controlled in test solution. The complexing agent is added in appropriate molar concentration to obtain the necessary molar ratios in the different complexes and to balance with other additives to ensure that all the reactions are performed optimally. Moreover, the complexing agent should be chosen with the particular metallic cation to be used in mind, to ensure that any potentially undersirable side effects such as too strong complexing of the metal ion are avoided.

The stability constant of the chelate-Me-complex has to be high enough to compete with other possible complexing agents in the test solution, for example the signal-forming boronic acid conjugate, but not so strong that the availability of the metal cation as precipitating agent is reduced or prevented.

Many chelating ligands may be used including ethylene-, propylene-, or butylene-diamine or analogues thereof, glycine, aspartate, nitriloacetate, histidine and picolinate. Several other natural or synthetic chelators such as carbohydrates, organic acids with more than one coordination group, aminoacids, peptides, phenolics and such like, may also be used but some of these are not preferred due to their ability to form complexes with boronic acid, i.e. salicylates, oxalates, carbohydrates such as sorbitol and tartrate, thereby competing with glycated protein for the binding to the signal-forming boronic acid conjugate.

Multidentate chelating ligands such as EDTA (ethylendiaminetetraaceticacid), CDTA (trans-1,2-diaminocyclohexane-N,N,N',N'-tetraaceticacid), EGTA (ethyleneglycol-o,o'-bis (2-amino-ethyl) -N,N,N',N'-tetraaceticacid), DTPA (diethylenetriaminepentaaceticacid) etc. may also be used but in certain situations may be less preferred due to their very strong complexing ability with metal ions resulting in highly reduced protein precipitation. Ammonium acetate buffer containing zinc ions and glycine is an example of a preferred combination.

Different complexing agents may be preferred in different embodiments of this invention. Complexing agents such as EDTA and DTPA are conveniently used, but their concentration must be carefully adjusted when combined with metallic cations used for protein precipitation. Citric acid and oxalic acid are less preferred due to interaction with boronic acid residues. Heparin and fluoride ions are other examples which may be used.

Precipitates obtained by precipitation from homogeneous solutions, such as by the use of organic solvents or metallic cations, can be totally or partially separated by means of centrifugation or filtration or by other techniques well known in the art.

Filter membranes or TLC-systems can also be used for the separation of the hemoglobin optionally with haptoglobins, antibodies or immunoreactive fragments thereof immobilized thereon to bind the protein being assayed, such as in a dipstick or multilayer film format.

Separation of the protein being assayed by means of centrifugation followed by separation of the precipitate from the supernatant is one of the preferred methods. Alternatively filtration may conveniently be used, and, this may be carried out either vertically to the filter surface through the filter, or tangentially or radially within the filter in a one-dimensional or two-dimensional separation method.

Thin layer chromatography methods can also be used. For example by application of the sample to a suitable chromatography medium, e.g. a test strip or gel, and application of reagents and washing solutions, for example directly to the site of application of the sample or by elution.

In further embodiments, the protein may be precipitated from solution directly onto or into a filter or other solid phase chromatography medium, in which case the precipitate may be deposited on or into the solid phase subsequent to or simultaneously with the formation of the precipitate. The reagents may be applied to a porous solid phase medium prior to, simultaneously with or after the precipitation step. Thus for example, reagents such as precipitating agents, the signal forming agents e.g. boronic acid reagent, hemolysing agents, complexing agents or other reagents, in any preferred combination, may be carried in or on the solid phase medium preferably in a dry form. Such reagent-carrying solid phase media form further aspects of the invention. The solid phase media may optionally be washed or an eluant solution may be eluted through the precipitation area.

For the performance of an albumin assay according to the invention, ligands immobilized on a solid support (e.g. beads of cross-linked agarose, dextran or polyacrylamide) may conveniently be used. Such immobilized ligands, e.g. octylamine, benzylamine, bromosulphophthalein-glutathione, N-(3-carboxypropionyl)aminodecane, Cibacron blue F3GA, deoxycholic acid, glycocholic acid, Procion Red HE3B, and N-pyromellitylaminodecane, are available commercially. The separation of albumin may also be effected using precipitating agents such as caprylic acid, capric salts, Rivanol (2-ethoxy-6,7-diaminoacridine lactate) and basic dextran. Albumin and other blood proteins can also be precipitated using various metal ions (e.g. Hg, Cd, Cn, Zn, etc) although some of these may be relatively specific. Moreover organic solvents, in the case of albumin low polarity solvents such as chloroform or alcohols (such as butanol or higher alkanols) may be used. For precipitation of blood proteins in general, agents such as ammonium sulphate, sodium sulphate and polethylene glycol may be used.

Where the protein being assayed is carried by cells within the blood, a lysing agent should be used to ensure a good chemical contact between the glycated protein and the first signal forming agent; a number of reagents and methods are generally known in the art and may be used, including hypotonic hemolysis, the use of detergents such as non-ionic polyethylene glycol ester or polyoxyethylene sorbitol ester derivatives, e.g. the "Tween" series, and polyoxyalkylphenol derivatives, e.g. the "Triton" series, cholates, sodium dodecylsulphates, guanidine, heating, sonication, or any combinations thereof.

The first signal forming agent may be contacted with or mixed with optionally hemolysed blood, plasma or serum samples or with proteins isolated from such samples, e.g. in an assay buffer solution, subsequently to or simultaneously with the optional hemolysis treatment step.

A number of assay buffers can be used, among them phosphate-buffers and other buffer solutions capable of maintaining the pH of the reaction mixture at a suitable pH. The preferred pH range of the assay is 7.5–10.0, but the desired pH is dependant upon the additives, buffer salts used and the $pK_a$ value of the signal forming agent where this is a reagent which, like the boronic acid derivatives, conjugates reversibly with the glycated protein. There is some evidence that buffers containing amine may serve to strengthen the dihydroxyboryl-cisdiol interaction, or to lower the apparent pKa value of the borate. Due to this fact buffers such as serine, glycine, Hepes (4-(2-hydroxyethyl)-1-piperazine-ethanesulphonic acid), ammonium acetate, morpholine and taurine are preferred. To further promote the interaction between dihydroxyboryl and cis-diol residues, additives such as divalent cations, detergents and chaotrophic agents may be used to reduce charge repulsions, solubilize target molecules, limit hydrophobic interations and increase the accessability of the diols in the glycated proteins. However, certain buffers, like Tris and ethanolamines, should be avoided due to the fact that these buffer compounds can complex borate and block diols from binding. Certain buffer/additive combinations, like phosphate-zinc, are also unfavourable because of the possible formation of insoluble compounds like $Zn_3(PO_4)_2$.

If in the method of the invention the protein under assay is hemoglobin, we have found that it is advantageous to use a stabilizer reagent, e.g. a salt having a stabilizing anion, ligands known to combine with ferrihemoglobin, agents which modify the absorption characteristics of hemoglobin (e.g. deoxygenating agents such as dithionite), redox mediators (such as methylene blue), etc, to stabilize the color of the hemoglobin. Thus for example nitrate salts may be used in this regard; further or optionally additional examples include azides, cyanoferrates, cyanides, fluorides, formates, thiocyanates, acetates, EDTA, ammonia, imidazole, nitric oxide, picoline, hydrosulphide, dithionite and methylene blue.

The method of this invention relies in preferred embodiments on binding between a boronic acid derivative and cis-diol moieties in GBPs—this binding is generally influenced only to a very little extent by temperature variations, especially within the ambient range.

The method of the invention involves the assessment or quantitation-of-the-said signal-forming agents (i.e. a signal-reading step) and optionally also of the total content of the protein under assay in both the glycated and non-glycated forms.

The assessment of the signal forming agents bound to or separated with the protein may be achieved by means of conventional chemical equipment commonly used for measuring enzymatic activity, fluorescence, radioactive radiation or optical density (absorbance), depending on the chemical nature of the signal forming label. Colour or fluorescence on a solid phase surface can readily be measured by means of reflectometry, which is in general use in clinical chemistry. On a dipstick or filter format or other practical solid phase format, hemoglobins and/or fluorescent or coloured signal forming agent:protein conjugates may be assessed directly on the surface. Alternatively, the precipitated or immobilized protein and/or the signal forming agent:protein conjugates may be redissolved and measured in solution.

Similarly, signal-forming conjugates having an enzymatic activity may be assessed in immobilized or dissolved or redissolved form by means of enzymometric technology well known in the art. So also with radioactive conjugates, which may be estimated using well known radiometric methods.

Where the protein under assay, like hemoglobin, has a pronounced absorption maximum in its UV-vis-IR spectrum the total concentration of its glycated and non-glycated forms may be determined by measuring absorption at the appropriate wavelength. If other components of the sample also show any significant absorption at this wavelength than such measurement will of course have to be carried out on the protein after its separation from such components, e.g. after separation using reagents which effectively do not participate or immobilize the components which would interfere with such absorption measurements. Alternatively, and preferably for proteins other than hemoglobin, a second signal forming agent may be used in the assay method, this second agent being one which will bind or otherwise conjugate to the protein under assay in both its glycated and non-glycated forms and which forms a signal differentiable from that of the first signal forming agent. The signal forming moiety may be any of those described above, e.g. a radiolabel, a chromophore, a fluorophore or an enzymatically active moiety. For ease of operation of the assay method, the signal forming moiety should preferably be of the same nature as that in the first signal forming agent so that the signals indicative of total and glycated protein content may be read out using the same manner of equipment. Particularly preferably the second signal forming agent is one which labels the protein with a chromophore having an absorption maximum at above 600 nm as in this way the signal can be read out for proteins other than hemoglobin without the need to remove any hemoglobin separated with the protein under assay. It should be noted that where a second signal forming agent is used it is not necessary that its binding properties should be specific for the protein under study; however if it does bind to other blood proteins which are present in non-negligible proportions relative to the protein under assay then the separation step in the method of the invention should be such as to separate the protein under assay from such other proteins. Where it is desired that the second signal forming agent should bind specifically to the protein under assay then labelled monoclonal or polyclonal antibodies or antigen binding fragments thereof specific for the protein under assay, in both its glycated and non-glycated forms, may conveniently be used.

Thus if total protein and glycated protein are labelled with spectrometrically distinguishable chromophores or, as is the case with hemoglobin total protein and first agent-labelled glycated protein have spectroscopically distinguishable chromphores, the concentration of both glycated and non-glycated protein under assay may be determined by means of absorption at the relevant wavelengths in the reaction mixture prior to or after the separation step. If fluorophores are to be quantitated in the presence of hemoglobin, excitation and emission wavelengths outside the absorption wavelengths of hemoglobin are preferred. Similarly, if a chromophore is used, an absorption wavelength outside that of hemoglobin is preferred, However, if necessary a partial interference from hemoglobin can be accepted and be corrected by calculations based on measurements at more than one wavelength.

In one embodiment of this invention, the separated protein is isolated on microbeads and/or a filter or other solid phase, followed by reflectometric quantitation of the glycated protein labelled with a first label and of the optionally labelled total protein, e.g. by light absorption measurements, or by measurements of fluorescence.

In further embodiments of this invention, samples or aliquots of blood hemolysate, plasma or serum depleted with respect to several or most or all other proteins reactive to boronic acid residues or salts thereof are used, e.g. erythrocytes can be washed before hemolysis in order to remove plasma proteins before the analysis of glycated hemoglobins or centrifigution or filtration may be effected in whole blood samples to remove cells before analysis. Alternatively, optionally hemolysed blood can be exposed to an ion exchange solid phase separator to remove all proteins with isoelectric points below and/or above that of the protein under assay. This purification can optionally be a part of the apparatus or kit for the performance of the method of this invention.

In a special embodiment of this invention, the amount of the first signal forming agent which is bound to the protein under assay in the presence and absence of a competing compound is measured. The competing compound can be any cis-diol containing molecule, e.g. sorbitol or mannitol, or boronic acid containing molecules with no signal forming activity.

In another special embodiment of this invention, the amount of the first signal forming agent present, either in the reaction mixture and/or in the separated fraction before and subsequent to the separation of the protein under assay, is measured making it possible to calculate the fraction of the signal forming agent removed by binding to that protein.

Since this invention may rely on a rather low binding strength (cf the association constant of $10^3$ to $10^5$ mol$^{-1}$l between cis-diol moieties and boronic acid residues), a direct stoichiometric binding between glycated protein and such signal forming boronic acid derivatives may not take place.

To a minor extent, free carbohydrates in blood may compete for boronic acid derivatives. These effects are diminished by the use of an excess of the signal forming boronic acid derivatives. A twenty times molar excess (relative to the proteins conjugable with the boronic acid derivative) is convenient, but higher and lower ratios can also be used, depending on which embodiment of this invention is used. Of course there will be a background signal depending on the efficiency of the separation techniques used. If a very efficient separation system is used, a higher excess can be used. If very high reactant concentrations cannot be used, the concentration of glycated protein should be calculated by reference to measurements made on standard compositions having known concentrations of glycated protein. The use of such standards is very common in clinical laboratory medicine.

This invention also provides a reagent composition or kit for the performance of the described method, said reagent comprising: a first signal forming agent capable of labelling a glycated blood protein; a liquid phase separating agent capable of precipitating said protein in its glycated and non-glycated forms; optionally a second signal forming agent capable of labelling said protein in its glycated and, non-glycated forms; and, optionally, buffer and/or stabilizer and/or lysing reagents, at least one of said first agent and said separating agent being substantially specific for said protein.

Viewed from another aspect the invention also provides apparatus for performing the method of the invention, said apparatus comprising: means for abstracting a blood sample; means for contacting said blood sample with the following agents
   (i) optionally, a hemolysing agent,
   (ii) a first signal forming agent (as hereinbefore defined),
   (iii) a liquid phase separating agent capable of precipitating a blood protein in its glycated and non-glycated forms,
   (iv) optionally, a second signal forming agent (as hereinbefore defined),
   (v) optionally, a stablilizer (as hereinbefore defined),
   (vi) optionally, a buffer,
individually or in one or more combinations thereof; and means, e.g. spectrometer means, for assessing the signal forming agents bound to blood proteins separated by said separating agent and optionally for spectrometrically assessing one or more blood proteins (e.g. hemoglobin) separated by said separating agent but substantially unbound by said signal forming agents. Particularly preferably the apparatus comprises a blood sampling device, means for passing a blood sample into a reaction chamber containing a solid phase arranged to receive separated protein, means for introducing reagents into said chamber, and a spectrometer arranged to detect photon emission from or absorption by proteins separated on said solid phase at at at least one and preferably at least two preset wavelengths.

The following examples and preparations are provided only by way of non-limiting illustration of the invention:

EXAMPLES

PREPARATIONS

Preparatory Example 1

1. N-(RESORUFIN-4-CARBONYL) -PIPERIDINE-4-CARBOXYLICACID CONJUGATE WITH M-AMINOPHENYL BORONIC ACID

Solution A: 2 mg RESOS (N-RESORUFIN-4-CARBONYL)-PIPERIDINE-4-CARBOXYLIC ACID-N'-HYDROXYSUCCINIMIDE ESTER) was dissolved in 0.5 ml dimethylsulphoxide.

Solution B: The hemisulphate salt of m-aminophenyl boronic acid was dissolved 15 mg/ml in 0.1 M sodium carbonate buffer, pH 8.0. pH was adjusted to 8.0.

0.5 ml solution A was added to 2 ml of solution B. The mixture was incubated at ambient temperature for 12 hours. Purification was performed by HPLC.

Preparatory Example 2

2. FLUORESCEIN ISOTHIOCYANATE (FITC) CONJUGATE WITH AMINOPHENYL BORONIC ACID

Solution A: 3.9 ml mg of FITC was dissolved in 1 ml dimethylsulphoxide.

Solution B: The hemisulphate salt of m-aminophenyl boronic acid was dissolved 1.86 mg/ml in 0.2 M carbonate buffer, pH 9.5

1 ml solution A was added s lowly to 10 ml solution B with constant stirring. The mixture was allowed to react for a minimum of 2 hours at ambient temperature, and the FITC-aminophenyl boronic acid conjugate was purified by HPLC.

Preparatory Example 3

3. IODINE-125-LABELLED BORONIC ACID CONJUGATE

A: Aminophenylboronic acid (APBA) 10 mg/ml in 50 mM Na-phosphate, pH 7.5 was reacted with Bolton-Hunter (BH) reagent 14.2 mg/ml in DMSO. BH was slowly added to the APBA up to an equal volume part. The solution was incubated for 1 hour at ambient temperature.

B: The reaction product was separated on a reversed phase column with a gradient of methanol in water with 0.1% trifluoroacetic acid (TFA).

C: The isolated BH-APBA reaction product was labelled with $^{125}$I—NaI by the chloramine-T method. 0.5 ml of BH-APBA fraction was added to 0.1 ml 0.25 M Na-phosphate pH 7.5 and the pH was adjusted to 7.5. 10 $\mu$l $^{125}$I—NaI, 100 $\mu$Ci was added in addition to freshly prepared 0.3 ml chloramin-T (10 mg/ml) in 0.25 M Na-phosphate pH 7.5, and the mixture was incubated for 1 min.

D: The reaction was stopped by the addition of 0.3 ml Na-bisulfite (24 mg/ml) in 0.25 M Na-phosphate pH 7.5.

E: Labelled BH-APBA was isolated by reversed phase chromatography by methanol gradient in water with 0.1% TFA.

Preparatory Example 4

4. BORONIC ACID CONJUGATE WITH ALKALINE PHOSPHATASE 10 mg alkaline phosphatase, depleted with respect to boronic acid reactive enzyme molecules by passing through a column of agarose with immobilized phenyl boronic acid residues, is mixed with 30 times molar excess of bis-(sulfosuccinimidyl) suberate in carbonate buffer pH=8.5 and is left to react for 120 minutes at room temperature, followed by the addition of 100 times molar excess of monoethanolamine. 4 hours thereafter, the enzyme conjugates are purified by gel chromatography.

EXAMPLES DEMONSTRATING NEAR SPECIFIC PRECIPITATION OF HEMOGLOBIN FROM WHOLE BLOOD-HEMOLYSATES

Metallic-cations:

Solution A: Whole blood hemolysate diluted in 50 mM Ammonium acetate pH 8.0 to a final concentration of 6.4 mg hemoglobin/ml.

Solution B: Cu(SO$_4$) dissolved in water to a concentration of 10 mM Cu$^{2+}$

Solution C: Zn(Cl)$_2$ dissolved in water to a concentration of 10 mM Zn$^{2+}$

Preparatory Example 5

40 $\mu$l solution B was added to 200 $\mu$l solution A. The mixture was incubated at ambient temperature for 5 minutes and the hemoglobin precipitate separated by centrifugation.

Examples or further reagents for use in the methods of the invention.

Preparatory Example 6

40 $\mu$l solution C was added to 200 $\mu$l solution A. The mixture was incubated at ambient temperature for 5 minutes and the haemoglobin precipitate separated by centrifugation.

EXAMPLES OF FURTHER REAGENTS FOR USE IN THE METHODS OF THE INVENTION

Reagent Example 1

Phenoxazine:boronic acid conjugate for use as a first signal forming agent

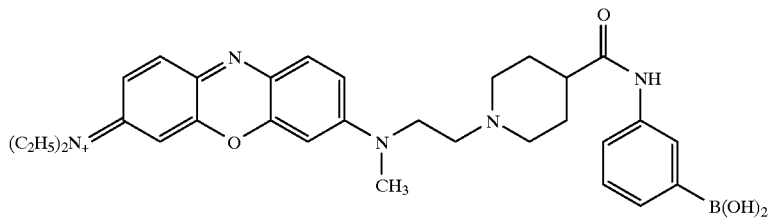

The synthesis of this agent, which has an absorption maximum above 600 nm, is described in our copending British Patent Application.

Reagent Example 2

Cr (III)-tetracarboxyphenylporphyrin
This, a second signal forming agent for albumin assays, is available from Porphyrin Products, USA, and is formulated in aqueous solution buffered to pH 9 with 0.25M ammonium acetate.

Reagent Example 3

Bromophenol Blue
This is widely available commercially and is formulated for use as a second signal forming agent for albumin assays buffered to pH 7.5 with 50 mM sodium phosphate.

Reagent Example 4

Precipitating agent for albumin assay
5% (w/v) of Rivanol in assay buffer (0.25 M ammonium acetate, 0.05% Triton X-100, pH 8.0). (This may form about 5–20% (v/v) of a total assay reagent composition comprising assay buffer with signal forming agents dissolved therein). Buffering may also be to pH 9.0.

Reagent Example 5

Albumin immobilizer
Polystyrene latex particles of an average size ranging from 0.05 to 1 $\mu$m are used for the preparation of antibody-latex conjugates. To 2 ml of the latex suspension in 0.15 M NaCl (50 mg/ml) 2.6 mg $\epsilon$-aminocaproic acid and 5 mg of 1-ethyl-3-(3-dimethylaminopropyl)carbodiimide-HCl (EDC) are added. The reaction is allowed to proceed for 3 hours at 4° C. and the solution is then dialyzed overnight in 0.15 M NaCl and the activated particles are collected by centrifugation. 20 mg antibody, depleted of boronic acid reactive sites, and 5 mg EDC in 2.5 ml of 20 mM sodium phosphate buffer, pH 7.0, are added to the precipitated particles. The reaction mixture is then rotated for 12 hours and unreacted active sites blocked with appropriate reagents. Finally the particles are washed and collected by centrifugation.

Reagent Example 6

Albumin immobilizer
Filter materials activated by conventional methods, including cyanogenbromide, carbodiimides, N-hydroxysuccinimides, bis-oxiranes and hydrazines, all well known in the prior art, are used as solid supports for immobilization of an anti-albumin antibody, previously depleted of boronic acid reactive sites.

This activated membrane is mounted in a suitable filter holder and 100 $\mu$l antibody solution of 2–300 $\mu$g protein per ml immobilization buffer, 50 mM sodium phosphate buffered saline, pH 7.3, is then passed through the filter at a controlled flow rate. Blocking of remaining activated sites on the filter is performed by passing blocking solutions, such as 0.5 M Tris buffer, pH 8.5, or 1 M ethanolamine, pH 9.5, through the filter membrane.

Reagent Example 7

Albumin immobilizer
Expoxy-activated filter materials formed by reaction with the bis-oxirane, 1,4-bis-(2,3-epoxypropoxy)butane are used as a solid support, prepared immediately before use according to methods well known in prior art. The filter is immersed in a solution of benzylamine in 50 mM sodium phosphate buffer, pH 7.5, and incubated for 12 hours at 40° C. under constant agitation. The concentration of benzylamine may be varied, but 50 mM has been found to be appropriate for immobilization and blocking of the active groups on most filters.

Reagent Example 8

Albumin immobilizer
Expoxy-activated filter materials formed by reaction with the bis-oxirane, 1,4-bis-(2,3-epoxypropoxy)butane are prepared. The disodium-salt of iminodiacetic acid is dissolved in 2 M sodium carbonate solution to a final concentration of 0.2 mg chelate per ml buffer, and then added to the preactivated filter material. The reaction is performed at 65° C. for 24 hours and the filters then washed with an excess of distilled water. To prepare the "active" metal chelate, the filter is immersed in a metal salt solution containing 1 mg/ml zinc chloride or copper sulphate, depending on the intended assay protein. Finally, the filter is washed in excess distilled water to remove free, unchelated metal ions.

Reagent Example 9

Boronic acid filter for separation of glycated proteins
Separation of glycated proteins from a test sample may be achieved by using a separation device including a filter modified with amino-phenyl-boronic acid or optionally another boronic acid containing moiety, where the boronic acid containing residue is covalently bound to the filter surface exposing the boronic acid group to the test sample passing through. The filter used for this application is preactivated for binding primarily to amino groups (Immunodyne (PALL), Immobilon (Millipore)). Aminophenylboronic acid is dissolved in a 0.2 M sodium-phosphate buffer, pH 7.5–8, into which the membrane is immersed. Non-reacted groups on the filter are blocked by addition of a 10 % monoethanolamine solution at pH 9. Alternatively the filter may be blocked by a solution of casein depleted of glycated protein by passage through a column containing a boronic affinity gel (Glyco-Gel B, Pierce). This yields a filter which has a low non-specific protein binding. Separation is performed at basic pH (pH 8–9) in a buffer suitable for the binding of boronic acid to the glycated part of the proteins. The device for separation consists of active filter in contact with an absorbent pad which draws the test sample through the active filter, removing all but the glycated proteins from the filter.

10 mg of monoclonal antibody obtained according to Reagent Example 10 are dissolved in 1 ml 0.1 M sodium phosphate buffer, pH 8.5. To this solution a 10 molar excess of

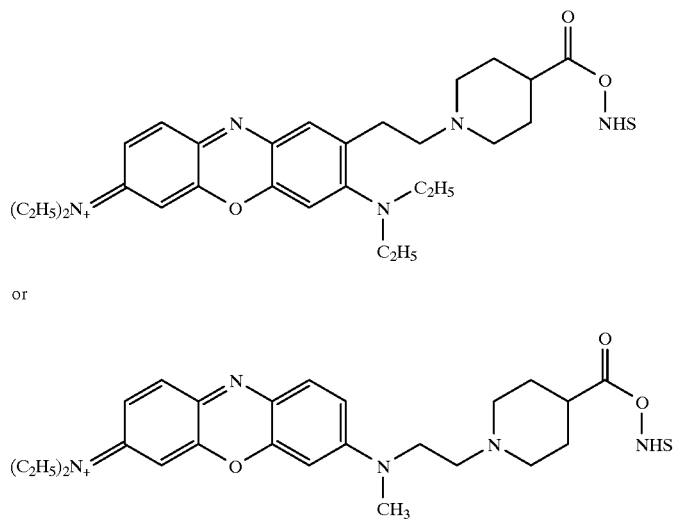

or

Reagent Example 10
Formation of antibodies reactive to the glycated segments of albumin
Using a glycated albumin antigen according to the method of Cohen et al, J. Immunol. Meth. 117: 121–129 (1989), monoclonal antibodies reactive to glycated albumin are obtained. For more specific immunization, the segment used for immunization is glucose-Lys525-Gln-Thr-Ala-Leu529, which is the most abundantly glycated residue in glycated albumin.

Reagent Example 11
Immobilizing agent (antibody) specific for glycated albumin
Separation of glycated albumin from a test sample may be achieved with a separation device including a filter modified with antibody or antibody fragments which react specifically with the principal site for glycation of albumin when this site is glycated (see Reagent Example 10). The filter used for this application is preactivated for binding primarily to amino groups (immunodyne (PALL), Immobilon (Millipore)). The antibody or antibody fragment is dissolved in a 0.2 M sodium-phosphate buffer, pH 7.5–8, into which the membrane is immersed. Non-reacted groups on the filter are blocked by addition of a 10% monoethanolamine solution at pH 9. Alternatively the filter may be blocked by a solution of casein depleted of glycated protein by passage through a column containing a boronate affinity gel (Glyco-Gel B, Pierce). This yields a filter which has a low nonspecific protein binding. The reactive part of the antibody is exposed to the sample passing through, thus immobilizing the glycated albumin.

Reagent Example 12
Monoclonal antibodies reactive to glycated albumin conjugated with an activated phenoxazine having a absorption maximum of about 645 nm NHS=N—hydroxysuccinimide ester grouping (synthesised as described in our copending British Patent application) is added, and the mixture is rotated for 1 hour at ambient temperature and finally dialyzed against a suitable buffer.

Reagent Example 13
Precipitating agents for all serum proteins, glycated or not
(A) Trichloroacetic acid (TCA) 0.76 M is prepared by dissolving 125 g TCA in 500 ml water and diluting to 1 L volumetrically.
Protein precipitation may be effected by thoroughly mixing 1 ml of a blood sample with a total protein concentration of 5–10 mg/ml with 0.25 of the TCA-reagent. The mixture is allowed to stand for 10 minutes and the precipitate is separated.
(B) For samples with total protein concentration of about 0.5 mg/ml a further precipitating agent is produced by dissolving 15.0 g of sulfosalicylic acid ($x2H_2O$) and 35.0 g of sodium sulfate (anhydrous) in water and diluting volumentrically to a final volume of 500 ml.
To a 0.5 ml sample, add 2 ml of the salicylic acid reagent, mix well, allow to stand for 10 minutes and separate the precipitate.

Reagent Example 14
Immobilizing agent for complement C3 (glycated and non-glycated)
Commercially available monoclonal antibodies reactive to human complement factor C3 (available from numerous commercial sources) are immobilized as described in Reagent Examples 6 and 11.

Reagent Example 15
Immobilising agent for carbonic anhydrase (glycated and non-glycated)

Commercially available monoclonal antibodies reactive to human carbonic anhydrase (available from numerous commercial sources) are immobilized as described in Reagent Examples 6 and 11.

Reagent Example 16
Phthalocyanine: boronic acid conjugate for use as a first signal forming agent
To a suspension of chloroaluminium phthalocyanine tetrasulphonate (60 mg, $6.7 \times 10^{-5}$ mol) in 2 ml benzene was slowly added dropwise and under constant stirring a 10-fold molar excess of oxalyl chloride, and the solution stirred at 25° C. under exclusion of moisture. After 12 h at this temperature, solvent was evaporated under reduced pressure and exclusion of moisture. Immediately thereafter 3-aminophenyl boronic acid monohydrate (20 mg, $1.35 \times 10^{-4}$ mol) in 1.5 ml 0.25 M sodium carbonate/sodium bicarbonate buffer (pH 9.0) was added to the resulting sulphonyl chloride and the solution was stirred at room temperature for 3–12 h. The boronic acid conjugates were isolated by reversed phase chromatography, mainly in the form of monophenyl boronic acid-functionalised dye.

EXAMPLES OF THE PERFORMANCE OF THE METHOD

Example 1
Glycated hemoglobin in whole blood using one dye and solvent precipitation
A sample of whole blood was hemolysed and diluted in a hemolysing assay-buffer, 100 mM Hepes with 0.05% Triton X-100, pH 9.0, to approximately 8 mg hemoglobin/ml. A mixture of 50% (v/v) butanol in ethanol and phenoxazine aminophenyl boronic acid conjugate described above in Reagent Example 1, is added to give a final butanol concentration of 9% (v/v), and a conjugate concentration of $1.6 \times 10^{-4}$ M. A precipitate is formed, and the precipitate is separated from the supernatant by centrifugation. The precipitate is redissolved in 0.05 M hydrochloric acid with 5% dimethyl sulphoxide and the concentration of haemoglobin and of the hemoglobin bound boronic acid phenoxazine conjugate are measured by absorption spectroscopy. The concentrations are calculated by interpolation on calibration curves obtained by the use of standard solutions of known concentrations of hemoglobin and glycated hemoglobin, and the percentage of glycated hemoglobin to total hemoglobin is calculated.

Example 2
Glycated albumin in whole blood using two dyes and rivanol precipitation (I)
10 µl of whole blood is mixed with 150 µl hemolysing assay buffer, comprising 0.25 M ammonium acetate, 0.05% Triton X-100, pH 9.0, but in addition comprising 100 nmol of the compound of Reagent Example 1 and 20 nmol Cr(III)-tetracarboxyphenylporphyrin.
18 µl of 5% (w/v) solution of Rivanol (2-ethoxy-6,9-diaminoacridine lactate) in assay buffer is added. The precipitate of albumin is separated by filtration, washed once, and the reflectance is measured at 645 and 450 nm by means of a Shimadzu Dual Wavelength Flying Spot Scanner CS 9000. The ratio of the reflectances at 645 and 450 nm is measured.
The assay is calibrated by the use of standard blood samples containing known fractions of glycated albumin quantified by classical colorimetry or by affinity chromatography or ion exchange chromatography.

Example 3
Glycated albumin in whole blood using two dyes and rivanol precipitation (II)
The procedure of Example 2 is repeated, substituting the compound of Reagent Example 16 for that of Reagent Example 1 and reading reflectance at 685 nm rather than 645 nm.

Example 4
Quantification of glycated albumin using immobilized antibodies and bromophenol blue
A filtration unit with immobilized monoclonal antibodies specifically reactive with glycated albumin is used (see Reagent Example 11).
10 µl of whole blood is mixed with 500 µl 130 mM NaCl, 20 mM sodium phosphate buffer, pH 7.5, comprising 0.05% Triton X-100 as a hemolyzing agent and 50 nM bromophenol blue. A part of this mixture, the volume depending on the binding capacity of the filter unit is contacted with the filter unit. The reflectance at 590 nm is measured using a reflectometer as in Example 2, the intensity being dependent on the amount of albumin reacted with the immobilized antibodies.
The fraction of glycated albumin is determined by reference to a measurement of blood albumin obtained independantly by conventional techniques.

Example 5
Quantification of glycated serum proteins
5 µl of serum (containing approximately 0.4 mg protein is mixed with 0.75 ml of the sulfosalicylic acid/sodium sulphate solution of Reagent Example 13B. After mixing and 10 minutes incubation, the precipitate is trapped by passage through a filter. Subsequently, 2 ml of a buffer, 0.25 M ammonium acetate, pH 9.0, with 0.05 % Triton X-100 and 100 nm of the compound of Preparatory Example 1 is passed through the filter. Subsequently, reflectance at 575 nm is measured by a Shimadzu dual wavelength flying spot scanner CS 9000. The reflectance intensity is a function of the concentration of the glycated proteins in the test sample.

Example 6
Quantification of glycated complement factor C3 (I)
10 µl of whole blood is mixed with 150 µl hemolysing assay buffer, comprising 0.25M ammonium acetate, 0.25% Triton X-100, pH 9.0, and in addition comprising 100 nmol of the compound of Reagent Example 1.
An aliquot of the mixture is transferred to a filter according to Reagent Example 14. (The volume of the aliquot must be adjusted so that the total binding capacity of the filter is not exceeded). The filter is washed once, and the reflectance is measured at 645 nm with a Shimadzu Dual Wavelength Flying Spot Scanner CS9000. The reflectance signal is dependant on the concentration of glycated complement C3.

Example 7
Quantitation of glycated complement factor C3 (II)
The procedure of Example 6 is repeated, substituting the compound of Reagent Example 16 for that of Reagent Example 1, and reading reflectance at 685 nm rather than 645 nm.

Example 8
Quantification of glycated carbonic anhydrase
10 µl of whole blood is mixed with 150 µl hemolysing assay buffer, comprising 0.25 M ammonium acetate, 0.05% Triton X-100, pH 8.0, and in addition comprising 100 nmol of the compound of Reagent Example 1.

An aliquot of the mixture is transferred to a filter according to Reagent Example 15. (The volume of the aliquot must be adjusted so that the total binding capacity of the filter is not exceeded). The filter is washed once, and the reflectance is measured at 645 nm with a Shimadzu Dual Wavelength Flying Spot Scanner CS 9000. The reflectance signal is dependent on the blood concentration of glycated carbonic anhydrase.

Example 9

Analysis of glycated albumin using a all-albumin-binding filter (benzylamine filter) and boronic acid dye (I)

10 μl of whole blood is mixed with 150 μl hemolysing assay buffer comprising 0.25 M ammonium acetate, 0.05% Triton X-100, pH 9.0, and also comprising 100 nmol of the compound of Reagent Example 2 (thus making washing hemoglobin from the filter unnecesary). An aliquot of the resulting mixture is passed through the filter of Reagent Example 7. The reflection on the filter is measured at 645 nm by means of a Shimadzu Dual Wavelength Flying Spot Scanner CS 9000.

Example 10

Analysis of glycated albumin using a all-albumin-binding filter (benzylamine filter) and boronic acid dye (II)

The procedure of Example 9 is repeated substituting the compound of Reagent Example 16 for that of Reagent Example 2 and reading reflectance at 685 nm rather than 645 nm. The compounds of Reagent Example 2 or 3 may optionally be included as second signal forming agent.

Example 11

Glycated hemoglobin in whole blood using one dye; filter format

A sample of whole blood was mixed with a hemolyzing reaction-buffer containing 160 mM piperazine, pH 9.4, 0.07% Triton X-100, 9.4% ethanol (v/v), 9.4% butanol (v/v) and the compound of Reagent Example 16 in a concentration of $2.1 \times 10^{-5}$ M. The final hemoglobin concentration was approximately 2 mg/ml. The whole blood was hemolyzed, and a precipitate formed. The precipitated hemoglobin was separated by filtration. The reflectance was measured at 685 and 470 nm by means of a Schimadzu Dual Wavelength Flying Spot Scanner CS 9000. The ratio of the reflectances at 685 and 470 nm was calculated.

The concentrations were calculated by interpolation on calibration curves obtained by use of standard solutions of known concentrations of hemoglobin and glycated hemoglobin, and the percentage of glycated hemoglobin to total hemoglobin was calculated.

For all reagents to be used in quantification of glycated human proteins, it is advantageous if the reagents of biological origin are passed through a column containing a gel with immobilized boronic acid moieties, optionally treated with periodate or Endoglycosidase; in this way the analytical reagents are purified from moieties reacting with boronic acid groups.

As an alternative, the signal forming moieties can be constituted by radioisotopes, e.g. Iodine-125, fluorescent, chemoluminiscent or bioluminescent moieites.

We claim:

1. A method of assessing a glycated blood protein in a sample, said method comprising the steps of:

a) optionally hemolyzing said sample to liberate cell bound glycated blood protein;

b) separating said glycated blood protein and the corresponding non-glycated blood protein from said sample using a liquid phase precipitation agent, or means substantially specific for the protein being assessed;

c) contacting said non-immobilized separated proteins with a first signal forming agent capable of binding to said glycated protein with substantially higher binding affinity than for the corresponding non-glycated protein;

d) optionally, contacting said non-immobilized separated proteins with a second signal forming agent capable of binding to said glycated protein and to said corresponding non-glycated protein; and e) assessing the signal forming agents which have bound to said non-immobilized separated proteins or which have not bound to said glycated protein or said corresponding non-glycated protein;

with the proviso that where said glycated protein comprises glycated hemoglobin said first signal forming agent is a chromophore labelled boronic acid or salt thereof having an absorption maximum at above 600 nm.

2. A method as claimed in claim 1, wherein step (c) is effected using two different first signal forming agents, each substantially specific for a different glycated blood protein, and optionally step (d) is effected using two different second signal forming agents substantially specific for the same two different blood proteins.

3. A method as claimed in claim 1 wherein said first signal forming agent comprises a conjugate of one or more dihydroxyboryl residues, or salts thereof, linked to a signal forming label.

4. A method as claimed in claim 1 wherein precipitation is achieved by addition of metallic cations.

5. A method as claimed in claim 1 wherein precipitation is achieved by addition of an organic solvent or mixture of organic solvents, in a concentration which is able substantially specifically to precipitate the protein being assessed.

6. A method as claimed in claim 1 wherein precipitation is achieved by addition of binding proteins specific for the protein being assessed.

7. A method as claimed in claim 1 wherein the precipitation step takes place on or within a solid phase.

8. A method as claimed in claim 1 wherein the precipitate so formed is separated by means of a chromatography or filtration medium or by centrifugation.

9. A method as claimed in claim 1 wherein the second signal forming agent binds substantially specifically to said glycated and corresponding non-glycated protein.

10. A method as claimed in claim 1 wherein the second signal forming agent binds, non-specifically to blood proteins.

11. A method as claimed in claim 1 for the assessment of glycated albumin or glycated complement C3.

12. A method as claimed in claim 1 for the assessment of glycated albumin and glycated complement C3.

13. A method as claimed in claim 11 for the assessment of glycated albumin, wherein the second signal forming agent is selected from the group consisting of metal salts, metal chelates, anionic dyes, porphyrins and synthetic derivatives thereof, ponceau S, coomassie brilliant blue, bicinchoninic acid, and bromophenol blue.

14. A method as claimed in claim 12 for the assessment of glycated albumin, wherein the second signal forming agent is selected from the group consisting of metal salts, metal chelates, anionic dyes, porphyrins and synthetic derivatives thereof, ponceau S, coomassie brilliant blue, bicinchoninic acid, and bromophenol blue.

15. A method of assessing a glycated blood protein in a sample, said method comprising the steps of:

a) optionally hemolyzing said sample to liberate cell bound glycated blood protein;
b) separating said glycated blood protein and the corresponding non-glycated blood protein from said sample using a liquid phase precipitation agent, or means substantially specific for the protein being assessed;
c) subsequently contacting said non-immobilized separated proteins with a first signal forming agent capable of binding to said glycated protein with substantially higher binding affinity than for the corresponding non-glycated protein;
d) optionally, contacting said non-immobilized separated proteins with a second signal forming agent capable of binding to said glycated protein and to said corresponding non-glycated protein; and
e) assessing the signal forming agents which have bound to said non-immobilized separated proteins and which have not bound to said glycated protein or said corresponding non-glycated protein;
with the proviso that where said glycated protein comprises glycated hemoglobin said first signal forming agent is a chromophore labelled boronic acid or salt thereof having an absorption maximum at above 600 nm.

16. A method as claimed in claim 15, wherein step (c) is effected using two different first signal forming agents, each substantially specific for a different glycated blood protein, and optionally step (d) is effected using two different second signal forming agents substantially specific for the same two different blood proteins.

17. A method as claimed in claim 15 wherein said first signal forming agent comprises a conjugate of one or more dihydroxyboryl residues, or salts thereof, linked to a signal forming label.

18. A method as claimed in claim 18 wherein precipitation is achieved by addition of metallic cations.

19. A method as claimed in claim 18 wherein precipitation is achieved by addition of an organic solvent or mixture of organic solvents, in a concentration which is able substantially specifically to precipitate the protein being assessed.

20. A method as claimed in claim 16 wherein precipitation is achieved by addition of binding proteins specific for the protein being assessed.

21. A method as claimed in claim 15 wherein the precipitation step takes place on or within a solid phase.

22. A method as claimed in claim 15 wherein the precipitate so formed is separated by means of a chromatography or filtration medium or by centrifugation.

23. A method as claimed in claim 15 wherein the second signal forming agent binds substantially specifically to said glycated and corresponding non-glycated protein.

24. A method as claimed in claim 15 wherein the second signal forming agent binds non-specifically to blood proteins.

25. A method as claimed in claim 15 for the assessment of glycated albumin or glycated complement C3.

26. A method as claimed in claim 15 for the assessment of glycated albumin and glycated complement C3.

27. A method as claimed in claim 25 for the assessment of glycated albumin, wherein the second signal forming agent is selected from the group consisting of metal salts, metal chelates, anionic dyes, porphyrins and synthetic derivatives thereof, ponceau S, coomassie brilliant blue, bicinchoninic acid, and bromophenol blue.

28. A method as claimed in claim 26 for the assessment of glycated albumin, wherein the second signal forming agent is selected from the group consisting of metal salts, metal chelates, anionic dyes, porphyrins and synthetic derivatives thereof, ponceau S, coomassie brilliant blue, bicinchoninic acid, and bromophenol blue.

* * * * *